US010105555B2

(12) United States Patent
Ellsworth et al.

(10) Patent No.: US 10,105,555 B2
(45) Date of Patent: Oct. 23, 2018

(54) SYSTEM AND METHOD FOR DETERMINING RADIATION DOSE TO CIRCULATING BLOOD

(71) Applicant: THE JOHNS HOPKINS UNIVERSITY, Baltimore, MD (US)

(72) Inventors: Susannah Ellsworth, Baltimore, MD (US); Eric Ford, Baltimore, MD (US); Stuart A. Grossman, Towson, MD (US); Robert Hobbs, Baltimore, MD (US); Lawrence Kleinberg, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 47 days.

(21) Appl. No.: 15/115,153

(22) PCT Filed: Jan. 30, 2015

(86) PCT No.: PCT/US2015/013774
§ 371 (c)(1),
(2) Date: Jul. 28, 2016

(87) PCT Pub. No.: WO2015/116932
PCT Pub. Date: Aug. 6, 2015

(65) Prior Publication Data
US 2016/0339270 A1   Nov. 24, 2016

Related U.S. Application Data

(60) Provisional application No. 61/933,962, filed on Jan. 31, 2014.

(51) Int. Cl.
*A61N 5/10* (2006.01)

(52) U.S. Cl.
CPC ................................. *A61N 5/1071* (2013.01)

(58) Field of Classification Search
CPC .................................................... A61N 5/1071
See application file for complete search history.

(56) References Cited

U.S. PATENT DOCUMENTS

| 5,458,125 | A | 10/1995 | Schweikard |
|---|---|---|---|
| 2007/0088573 | A1 | 4/2007 | Ruchala |
| 2008/0292055 | A1 | 11/2008 | Boone |

OTHER PUBLICATIONS

International Search Report dated Aug. 28, 2015 from corresponding International Application No. PCT/US2015/013774; 2 pgs.

*Primary Examiner* — Mark R Gaworecki

(57) ABSTRACT

The present invention discloses systems and methods for calculating the radiation doses received by circulating blood cells. The present method may be applicable for calculating the radiation doses by circulating blood cells through any site in a patient. The present invention also discloses computer systems for calculating radiation doses received by circulating blood cells in a patient.

21 Claims, 6 Drawing Sheets

SYSTEM AND METHOD FOR DETERMINING RADIATION DOSE TO CIRCULATING BLOOD

CROSS-REFERENCE TO RELATED APPLICATIONS

This application claims benefit from U.S. Provisional Application 61/933,962, filed Jan. 31, 2014. This application is incorporated herein by reference for all purposes.

STATEMENT REGARDING FEDERALLY SPONSORED RESEARCH

N/A

BACKGROUND OF THE INVENTION

The present invention relates generally to systems or methods of using such systems to calculate the radiation dose received by circulating blood cells during a course of external beam radiotherapy. The present invention also discloses systems or methods of applying such systems to identify circulating blood as an organ at risk in radiation therapy.

Marked reductions in the lymphocyte count are common following therapy for malignant glioma and can have significant clinical consequences. Severe lymphopenia in this setting has been associated with serious opportunistic infections [Mahindra A K, Grossman S A. *Pneumocystis carinii* pneumonia in HIV negative patients with primary brain tumors. J Neurooncol 2003; 63(3):263-270; Meije Y, Lizasoain M, Garcia-Reyne A, et al. Emergence of cytomegalovirus disease in patients receiving temozolomide: report of two cases and literature review. Clin Infect Dis 2010; 50(12):e73-e76. doi: 10.1086/653011]. Perhaps more importantly, emerging data from patients with malignant gliomas and pancreatic cancer demonstrate that patients with severe treatment-induced lymphopenia have significantly worse survival and die from early tumor progression [Balmanoukian A, Ye X, Herman J, Laheru D, Grossman S. Effect of treatment-related lymphopenia on survival in newly diagnosed patients with adenocarcinoma of the pancreas. Clin Invest 2012; In press; Grossman S A, Ye X, Lesser G, et al. Immunosuppression in patients with high-grade gliomas treated with radiation and temozolomide. Clin Cancer Res 2011; 17(16):5473-5480. doi: 10.1158/1078-0432.CCR-11-0774; 10.1158/1078-0432.CCR-11-0774]. Interest in treatment-induced lymphopenia was sparked by a cluster of *Pneumocystis jiroveci* pneumonia cases, associated with extremely low CD4 counts, in patients treated with radiation therapy and steroids (without chemotherapy) for brain tumors (Mahindra A K, Grossman S A. *Pneumocystis carinii* pneumonia in HIV negative patients with primary brain tumors. J Neuro Oncol 2003; 63(3):263-270). This led to a prospective study of serial total lymphocyte and CD4 counts in brain tumor patients receiving radiation and corticosteroids. This demonstrated that CD4 counts were >450/μL in all patients before starting therapy, but that during treatment, approximately one-fourth developed CD4 counts <200/μL [Hughes M A, Parisi M, Grossman S, Kleinberg L. Primary brain tumors treated with steroids and radiotherapy: Low CD4 counts and risk of infection. Int J Radiat Oncol Biol Phys 2005; 62(5):1423-1426. doi: 10.1016/j.ijrobp.2004.12.085]. After temozolomide became standard therapy, a second study prospectively evaluated serial lymphocyte counts in high-grade glioma patients receiving radiation and temozolomide. In this study, over 40% of patients developed CD4 lymphocyte counts under 200/μL 2 months after completing treatment and over 70% had CD4 counts under 300/μL. Participants with CD4 counts <200/μL 2 months after initiating radiation and temozolomide had significantly worse overall survival than those with higher CD4 counts [Grossman S A, Ye X, Lesser G, et al. Immunosuppression in patients with high-grade gliomas treated with radiation and temozolomide. Clin Cancer Res 2011; 17(16):5473-5480. doi: 10.1158/1078-0432.CCR-11-0774; 10.1158/1078-0432.CCR-11-0774].

Although patients with malignant glioma receive a triad of lymphotoxic agents (corticosteroids, temozolomide, and radiation therapy), radiation may play an important role in lymphopenia. Lymphopenia following radiation therapy was first described in the early 20th century, only a few years after x-rays were discovered, and has since been documented to occur after either external beam radiotherapy or brachytherapy directed to virtually every part of the body [Shohan J. Some theoretical considerations on the present status of roentgen therapy. N Engl J Med 1916; 175:321-327]. Radiation can induce lymphopenia regardless of whether chemotherapy or steroids are given concurrently or whether bone marrow or lymphatic tissue is included in the field. For example, irradiation of the brain, which contains neither bone marrow nor lymphatic tissue, can cause over a 60% reduction in the lymphocyte count [MacLennan I C, Kay H E. Analysis of treatment in childhood leukemia. IV. The critical association between dose fractionation and immunosuppression induced by cranial irradiation. Cancer 1978; 41(1):108-111]. Furthermore, even radiation of extracorporeal blood in patients undergoing renal dialysis can result in profound and durable lymphopenia [Weeke E. The development of lymphopenia in uremic patients undergoing extracorporeal irradiation of the blood with portable beta units. Radiat Res 1973; 56(3):554-559]. These observations suggest that irradiation of circulating lymphocytes may contribute to the development of radiation-induced lymphopenia.

Calculating radiation dose to circulating blood is challenging and is affected by many parameters, including target volume size, radiation treatment technique, dose rate, total dose, fraction size, treatment time, the speed of circulating blood, and the presence or absence of major vasculature in or near the radiation field. Presently, although circulating blood cells are an organ at risk for toxicity due to radiation therapy, there are no commercially available systems to calculate the dose to circulating blood. Needed in the art are methods and systems for calculating the dose received by circulating blood during a course of external beam radiotherapy.

SUMMARY OF THE INVENTION

The present invention overcomes the aforementioned drawbacks by providing systems or methods of applying such systems to calculate the dose received by circulating blood during a course of external beam radiotherapy.

In one configuration, the present invention discloses a non-transitory, computer readable storage medium having instructions stored thereon that, when executed by a computer processor, cause the computer processor to receive medical imaging data from a subject including information about a treatment site receiving a dose of radiation, receive a plurality of subject/treatment-specific variables including at least two of a target volume size associated with the dose of radiation, a radiation treatment technique associated with the dose of radiation, a dose rate associated with the dose of radiation, a total dose associated with the dose of radiation, a fraction size associated with the dose of radiation, a treatment time associated with delivering the dose of radiation, a speed of circulating blood within the subject, and a presence of vasculature relative to the treatment site; and determine using the plurality of subject/treatment-specific variables a as quantity of radiation received by circulating blood within the subject when receiving the dose of radiation.

In one configuration, the present invention discloses a method of using the above system to calculate the dose received by circulating blood during a course of external beam radiotherapy. The method comprise the steps of obtaining medical imaging data of a site in a patient; creating a tumor volume within the site using the medical imaging data; determining a dose of radiation delivered to the site including the tumor volume and surrounding normal tissues; generating a three-dimensional dose grid for the site; using the three-dimensional dose grid for the site, calculating a distribution of radiation dose to a blood pool that is either within or transits through the site; generating dose volume histograms for the blood or its constituents as normal organs; and generating a report indicating the dose of radiation received by circulating blood using the quantification.

In one configuration, the present invention discloses a computer system for calculating radiation doses received by circulating blood cells in a patient, the computer system comprising an input interface unit to load pre-obtained medical imaging data of a site in a patient into the system and a processor. The processor is configured to carry on the steps of creating a tumor volume within the site using the medical imaging data, determining a dose of radiation delivered to the site using the tumor volume and surrounding normal tissues, and generating a three-dimensional dose grid for the site. The processor is also configured to carry out the steps of calculating a dose of radiation to a blood pool within or transiting through the site defining a radiation dose distribution to the blood volume considered as a whole. The system also includes a display to display the calculating radiation doses received by circulating blood cells in a patient.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
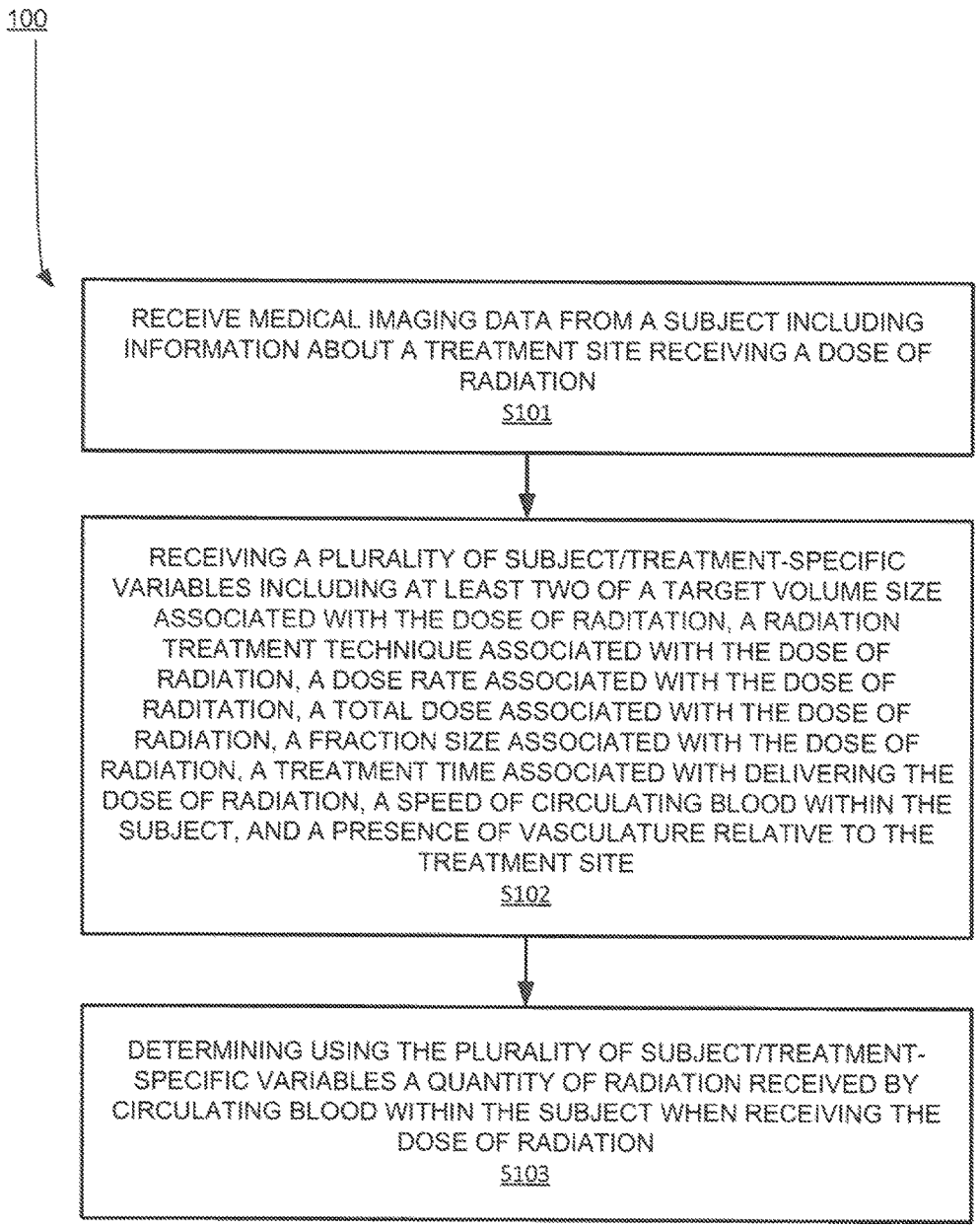
FIG. 1 is a flow chart setting forth the steps undertaken by a computer processor under instructions of computer readable storage mediums according to embodiments of the present invention.

External beam radiation frequently causes lymphopenia, which is associated with immunosuppression and decreased cancer control. This effect is probably due to irradiation of the circulating blood. However, to date circulating blood has not been considered as an organ at risk during radiation therapy, and no techniques are currently available to determine the radiation dose received by circulating blood during a course of external beam radiation therapy. Applicants have developed a method of calculating radiation dose received by circulating blood during external beam radiotherapy. Through the present method, Applicants have identified circulating blood as an organ at risk in radiation therapy.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The terminology as set forth herein is for description of the embodiments only and should not be construed as limiting of the invention as a whole.

As used herein, the term "subject" or "individual" refers to a human or other vertebrate animal. It is intended that the term encompass "patients."

As used herein, the term "the term "computed tomography" or "CT" refers to a technology that uses computer-processed x-rays, positron or single-photon emissions to produce tomographic images (virtual 'slices') of specific areas of the scanned object, allowing the user to see what is inside it without cutting it open. Generally, CT may refer to x-ray CT, because x-ray CT is the most common form of CT in medicine and various other contexts. Other types may also exist, such as positron emission tomography [PET] and single-photon emission computed tomography [SPECT]). CT produces a volume of data that can be manipulated in order to demonstrate various bodily structures based on their ability to block the x-ray beam. Although, historically, the images generated were in the axial or transverse plane, perpendicular to the long axis of the body, modern scanners allow this volume of data to be reformatted in various planes or even as volumetric (3D) representations of structures.

As used herein, the term "radiation therapy", "radiation oncology", or "radiotherapy", also abbreviated as XRT or DXT, refers to the medical use of ionizing radiation, generally as part of cancer treatment to control or kill malignant cells. Radiation therapy may be curative in a number of types of cancer if they are localized to one area of the body. It may also be used as part of adjuvant therapy, to prevent tumor recurrence after surgery to remove a primary malignant tumor (for example, early stages of breast cancer). Radiation therapy may be synergistic with chemotherapy, and has been used before, during, and after chemotherapy in susceptible cancers.

As used herein, the term "lymphocyte" refers to a type of white blood cell in the vertebrate immune system. Specifically, lymphocyte may be used as a landmark of the adaptive immune system.

As used herein, the term "radiation treatment plan" refers to the process in which a team consisting of radiation oncologists, radiation therapist, medical physicists and medical dosimetrists plan the appropriate external beam radiotherapy or internal brachytherapy treatment technique for a patient with cancer.

Typically, medical imaging (for example, x-ray computed tomography often the primary image set for treatment planning, magnetic resonance imaging excellent secondary image set for soft tissue contouring, and positron emission tomography less commonly used and reserved for cases where specific uptake studies can enhance planning target volume delineation) are used to form a virtual patient for a computer-aided design procedure. Treatment simulations are used to plan the geometric, radiological, and dosimetric aspects of the therapy using radiation transport simulations and optimization. For intensity modulated radiation therapy (IMRT), this process involves selecting the appropriate beam energy (photons, and perhaps protons), energy (for example, 6 MV, 18 MV) and arrangements. For brachytherapy, involves selecting the appropriate catheter positions and source dwell times (in HDR brachytherapy) or seeds positions (in LDR brachytherapy). Plans are often assessed with the aid of dose-volume histograms, allowing the clinician to evaluate the uniformity of the dose to the diseased tissue (tumor) and sparing of healthy structures.

The present invention generally applies to a mammalian species. In one preferred embodiment, the present invention applies to humans.

In one configuration, the present invention discloses a non-transitory, computer readable storage medium having instructions stored thereon that, when executed by a computer processor, cause the computer processor to determine radiation doses received by circulating blood within the subject when receiving the dose of radiation. FIG. 1 is a flow chart setting forth the steps according to some examples of the present invention. As shown in FIG. 1, the process begins with receiving medical imaging data from a subject including information about a treatment site receiving a dose of radiation (S101). Likewise, a plurality of subject/treatment-specific variables are provided to the system (S102). Some examples of subject/treatment-specific variables may include a target volume size associated with the dose of radiation, a radiation treatment technique associated with the dose of radiation, a dose rate associated with the dose of radiation, a total dose associated with the dose of radiation, a fraction size associated with the dose of radiation, a treatment time associated with delivering the dose of radiation, a speed of circulating blood within the subject, and a presence of vasculature relative to the treatment site, As described herein, the present invention may be implemented with any combination of the above-described variables, such as only one or two or even all of these or other variables. The medical imaging data and the plurality of subject/treatment-specific variables are then used as inputs to a model that, as will be described, allows the calculation of radiation received by circulating blood within the subject when receiving the dose of radiation.

In one configuration, the present invention discloses methods for calculating the radiation doses received by circulating blood cells such as lymphocytes. The present methods may be applicable for determining the radiation doses received by circulating blood cells through any site in a patient. In one embodiment, a suitable site in a patient may include head, heart, lung, and other tissues or organs. In one specific embodiment, a suitable site may be head.

Figure 2:
FIG. 2 is a flow chart setting forth the steps of methods for calculating radiation doses received by circulating blood cells during a course of external beam radiotherapy.

FIG. 2 is a flow chart setting forth the steps of methods for calculating the dose received by circulating blood during a course of external beam radiotherapy. As shown in FIG. 2, a method for calculating radiation doses received by circulating blood cells in a patient may include the steps of obtaining medical imaging data of a site in a patient (S201). Many medical imaging data may be suitable for the present invention. In one specific embodiment, one suitable medical imaging data may include either one of magnetic resonance imaging (MRI) data or computed tomography (CT) data. Thereafter, the processes includes creating a tumor volume within the site using the medical imaging data (S202), determining a dose of radiation delivered to the site using the tumor volume(S203), generating a three-dimensional dose grid for the site (S204). The process also includes using the three-dimensional dose grid for the site, calculating a mean dose to a blood pool within the site (S205) and quantifying a total volume of blood receiving radiation (S206).

For example, one may wish to calculate radiation doses received by circulating blood cells or more specifically to all lymphocytes, which may include reserves found outside the blood during initial radiation. Thereafter, report of radiation dose received by circulating blood may be generated (S207).

EXAMPLE

In one specific embodiment, one suitable patient may have at least one tumor at the site of interest in need of radiation therapy. The site of interest may include any suitable tissues or organs in a patient. In one embodiment, the site of interest may be head.

After medical imaging data, such as CT scan or MRI, of a site of interest is obtained, creating a tumor volume with the site using the medical imaging data. The tumor volume may be in any suitable shapes.

In one embodiment, the tumor volume may be spherical. In one specific example, the CT scan or MRI data may be loaded into a first program in a computer system, wherein a spherical tumor volume of the site is created. When the site of interest is head, the spherical tumor volume may be centered in the falx superior to the lateral ventricles. Applicants envision that many software programs may be used as the first program in the present invention. In one example, the first program may be a commercially available program. Specifically, the first program is the Pinnacle™ radiation treatment planning system (Version 9.0, Philips Inc., Madison, Wis.).

After the tumor volume of the site is created, a dose of radiation delivered to the site using the tumor volume may be determined. In one specific example, the dose to the site of interest may be calculated by using a software program, such as the first program. For example, three-dimensional dose grid for the site may be generated. In one specific example where head is the site of the interest, the entire site of interest may be delineated and a treatment plan may be then generated resulting in a calculation for the dose, for example, voxelized in 0.4 mm³ voxels. After the three-dimensional dose grid for the site of interest is generated—a mean dose to a blood pool may be calculated and a dose volume histogram may be generated. In one specific example, the three-dimensional dose grid for the site may be analyzed by using a software program, such as a second program. More specifically, the second program is an in-house software program written in MATLAB (version R2011b, Mathworks, Inc., Natick, Mass.).

Calculating radiation dose to circulating blood is challenging and is affected by many parameters, including target volume size, radiation treatment technique, dose rate, total dose, fraction size, treatment time, the speed of circulating blood, and the presence or absence of major vasculature in or near the radiation field. Presently, although circulating blood cells are an organ at risk for toxicity due to radiation therapy, there are no commercially available systems and methods to calculate the dose to circulating blood. Applicants create the above method by designing a mathematical model into the second program. The mathematical model may incorporate total radiation dose, fraction size, target volume size, radiation treatment technique, and dose rate as discontinuous variables in its first iteration.

In one embodiment of the present method, several treatment plans may be considered and analyzed. For example, when head is the site of interest, the present method may use a four-field conformal plan that treats the planning target volume (PTV) to a homogeneous dose. For comparison, a 3D-conformal plan using wedges and five fields may be calculated, and an intensity-modulated radiotherapy (IMRT) plan, for example that using a 2-cm wide sliding window, and an inverse planning approach may also be calculated. In each case of the present method, the dose may be extracted beam-by-beam for the plans other than IMRT and segment-by-segment for IMRT.

In one embodiment, the present method may use the dose to the brain during a normal course of radiation therapy (RT) as its input. The present method may then use calculate the associated dose to blood circulating through this radiation field.

In order to calculate radiation dose to circulating blood cells, one may need to make a few assumptions. For example, when head is the site of interest, the assumptions may include those as follow:

(a) 16% of cardiac output goes to the brain;
(b) blood flow is evenly distributed, flowing inferiorly to superiorly through the dose grid;
(c) blood flow velocity is 10 mm/s; and
(d) the total volume of blood is 5 L.

One further assumption may be that blood could pass through the beam multiple times but that during the duration of a single beam and/or segment, blood does not reenter the treatment field.

This latter assumption may break down with beam times that are longer than the 30-s heart-to-heart circulation time. However, Applicants found that this may only affect the calculations at the very lowest dose rates. Between beams and between treatment fractions, the blood may be considered to reenter the treatment field, and the cumulative dose may be calculated via a convolution of blood pool dose histograms. Within the MatLab code in the second program, one could control the dose rate, expressed in monitor units (MU)/min and the dose delivered per fraction by scaling the total number of monitor units delivered. The previous paragraphs already capture the essence of the program-voxelized dose grids are generated by Pinnacle; but they are static, while the blood is dynamic. Blood flows through the radiation treatment zone as radiation is delivered. In its simplest form, given (a) the length of treatment time (for each beam), (b) the flow rate of the blood through the site and (c) the size of the treatment site, the amount of blood transiting through the irradiated zone may be calculated: specifically, as the voxel of blood flows through an irradiated voxel, the dose received is incremented by the dose delivered during the time it takes for the blood to transit through the voxel. Each blood voxel is followed or moved incrementally in the direction of blood flow specific to the anatomical region under treatment until the treatment time ends or the blood voxel exits the site. The dose tally for each blood voxel, i, is the sum of doses received in the different physical voxels j through which the blood transited:

$$D_i = \sum_j \frac{dD_j}{dt} \cdot t_j,$$

wherein $dD_j/dt$ is the dose rate voxel j and $t_j$ is the time the blood took to transit through voxel j with beam on. For each beam, the process is repeated, but the total blood voxel dose from each beam or each fraction is convolved with the dose distribution obtained from previous beams or fractions (which supposes a known volume of blood and blood voxels).

Additionally, the cellular component of interest (lymphocytes) in the circulating blood may have reserves in the body that may be released subsequent to initial radiation and may be potentially by replenished; therefore a compartmental model which supplements the blood dose model to calculate dose distribution to the lymphocyte population including cells present in the blood initially as well as radiation treatment progresses which will be different from the generic blood volume dose distribution is desirable. The compartmental model assumes replenishment proportional to the reserve, meaning that it is characterized by a set of first order differential equations:

$$\frac{dN_k}{dt} = \sum_l a_{kl} N_l,$$

wherein N is the number of cells present in each compartment, k and $\alpha_{kl}$ is the coefficient of proportionality for cells to transfer between compartments; l iterates over all compartments These equations are solved numerically using the Runge-Kutta $4^{th}$ order method with adaptive step-size control:

$$N_{k(n+1)} = N_{k(n)} + \frac{1}{6}(k_{k0} + 2k_{k1} + 2k_{k2} + k_{k3})$$

where:

$$\begin{cases} k_{k0} = \Delta t \cdot \sum_l a_{kl} N_l \\ k_{k1} = \Delta t \cdot \sum_l a_{kl}\left(N_l + \frac{k_{l0}}{2}\right) \\ k_{k2} = \Delta t \cdot \sum_l a_{kl}\left(N_l + \frac{k_{l1}}{2}\right) \\ k_{k3} = \Delta t \cdot \sum_l a_{kl}(N_l + k_{l2}) \end{cases}$$

and $\Delta t$ is the time increment between each (n) and (n+1) time point.

A total volume of blood receiving radiation may be quantified. In one specific example, one may quantify a total volume of blood receiving any specific dose of radiation. For example, the specific dose of radiation may be 0.5 Gy.

The specific dose of radiation of 0.5 Gy may be chosen based on in vitro data on lymphocyte radiosensitivity that showed a D10 (dose required to reduce the surviving lymphocyte population to 10% of initial values) of ~3 Gy, a $D_{50}$ of ~2 Gy, and a $D_{90}$ of ~0.5 Gy [Nakamura N, Kusunoki Y, Akiyama M. Radiosensitivity of CD4 or CD8 positive human T-lymphocytes by an in vitro colony formation assay. Radiat Res 1990; 123(2):224-227].

The present method may be used to calculate the dose parameters for PTVs of any suitable sizes. In one specific example, the present method may be used to calculate the dose parameters for PTVs of two sizes: 2-cm diameter (4.2 cm³ volume) and 8-cm diameter (268 cm³ volume).

The present method may be applicable to calculate the dose parameters for plans administered at varying dose rates, for example 300, 600, and 1,200 MU/min, and various radiation techniques, for example IMRT and 3D-conformal.

After the calculation of radiation dose to circulating blood, a report of radiation dose received by circulating blood may be generated.

In one embodiment, one may model the radiation dose delivered to circulating blood during a typical partial intracranial field in an effort to determine the role of radiation in the observed lymphopenia.

For example, one may determine the effects on dose to circulating blood after varying different treatment-related parameters in the model.

Figure 3:
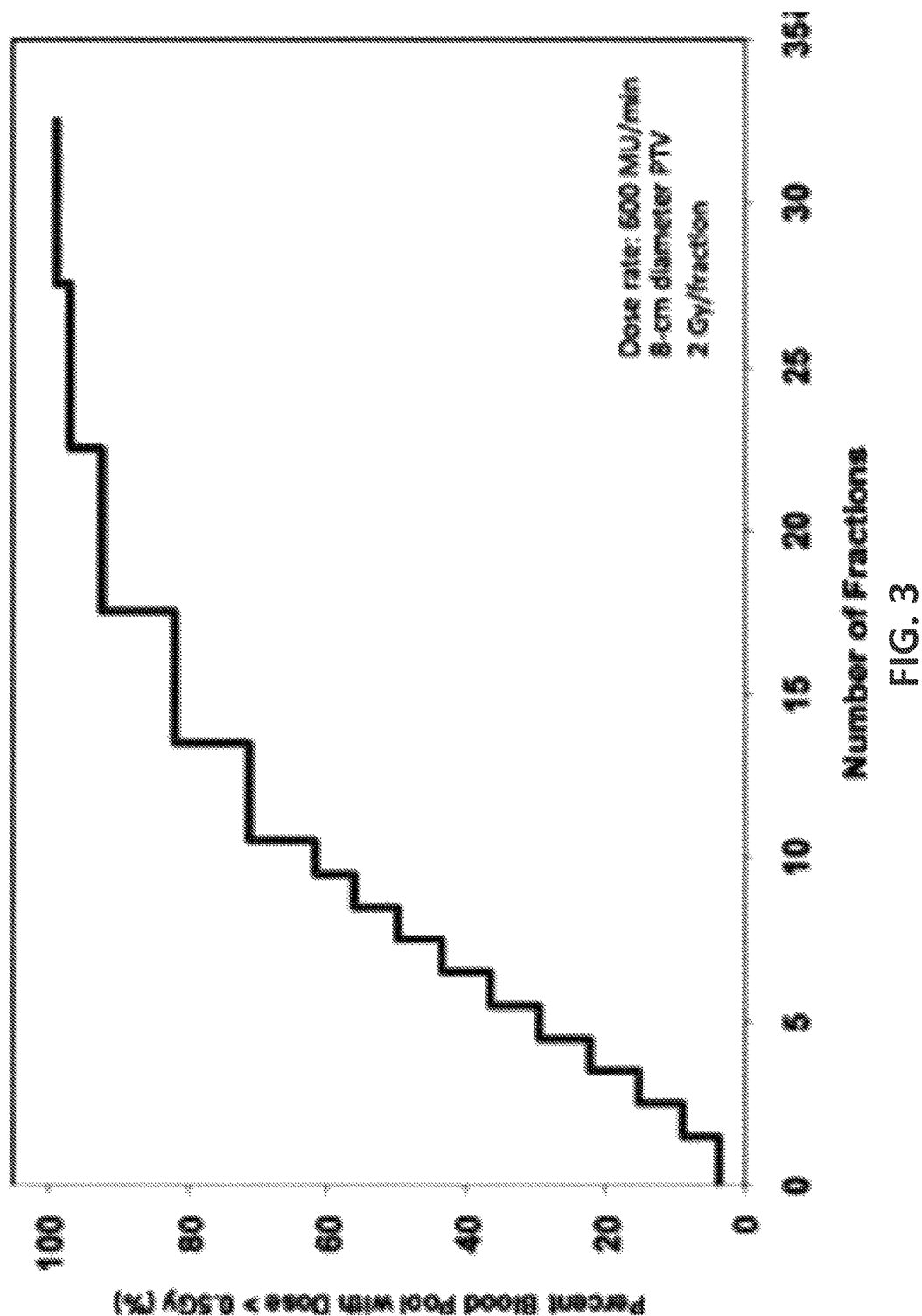
FIG. 3 is a graph showing percentage of blood receiving >0.5 Gy plotted against total dose/number of fractions administered. Dose rate=600 MU/min; PTV diameter=8 cm (volume=268 $cm^3$); 2 Gy/fraction.

FIG. 3 is a graph showing percentage of blood receiving >0.5 Gy plotted against total dose/number of fractions administered. Dose rate=600 MU/min; PTV diameter=8 cm (volume=268 cm³); 2 Gy/fraction.

As shown in FIG. 3, the result from the present method indicates that a single fraction (2 Gy) delivered 0.5 Gy to 4.6% of the total blood pool. After 10 fractions (20 Gy), 61.5% of the blood pool received 0.5 Gy, and after 20 fractions (40 Gy), 92.2% of the blood pool received 0.5 Gy.

By the end of a typical 60-Gy radiation treatment plan to the brain (2 Gy×30 fractions to an 8-cm diameter field), 98.8% of all circulating blood receives at least 0.5 Gy. Mean dose to the blood pool was 2.2 Gy for a 60-Gy course with a PTV of 268 cm² at a dose rate of 600 MU/min. According to the model, as the total dose and the number of fractions increase, the percentage of blood receiving 0.5 Gy increases rapidly.

Figure 4:
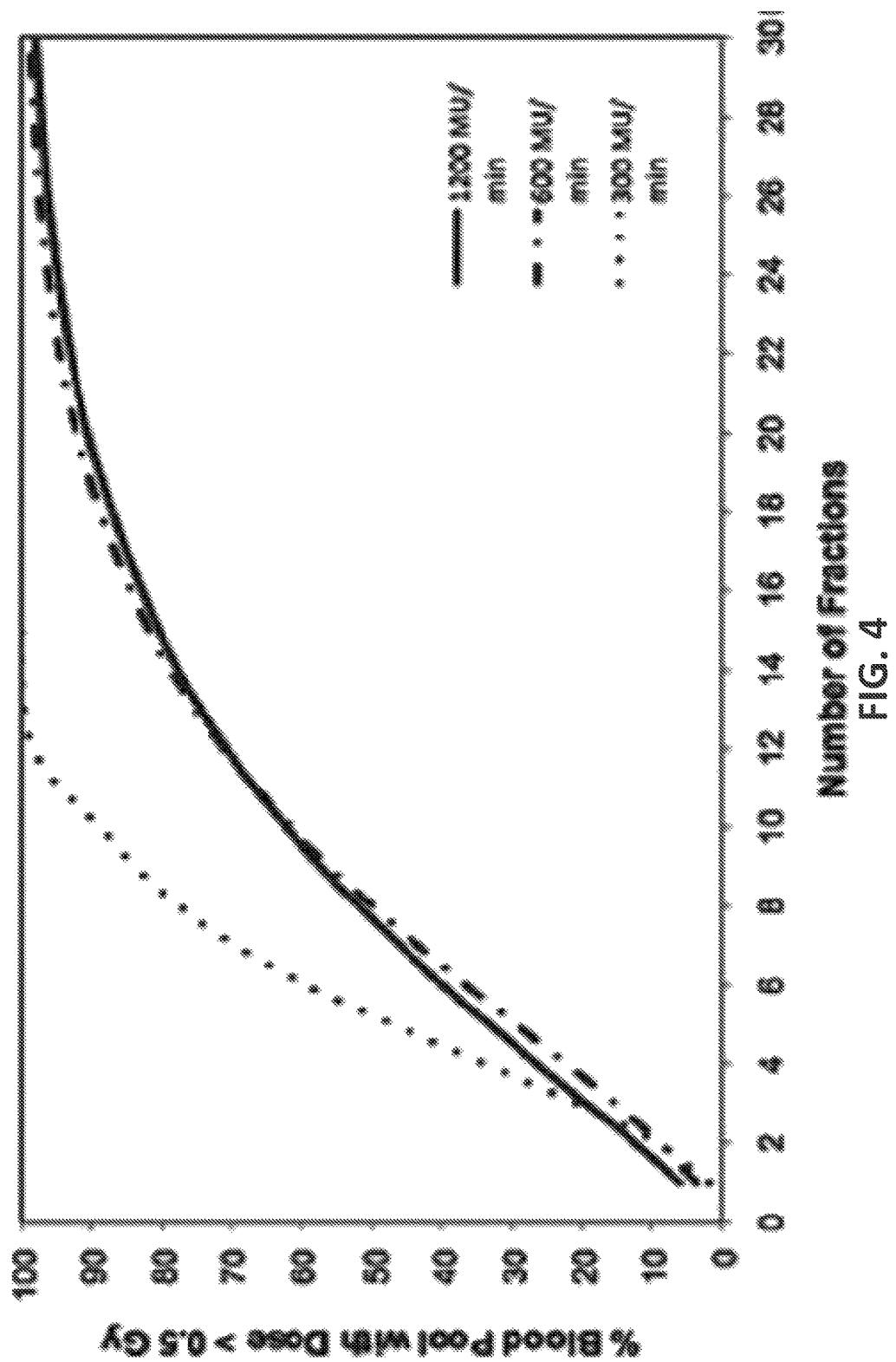
FIG. 4 is a graph showing percent of blood receiving >0.5 Gy with varying dose rates (300, 600, and 1,200 MU/min). PTV diameter=8 cm (volume=268 $cm^3$); 2 Gy/fraction.

FIG. 4 is a graph showing percent of blood receiving >0.5 Gy with varying dose rates (300, 600, and 1,200 MU/min). PTV diameter=8 cm (volume=268 cm³); 2 Gy/fraction.

As shown in FIG. 4, increasing the dose rate effectively shortens the treatment time, thereby reducing the number of lymphocytes passing through the radiation field. An increased dose rate (for example, a shorter beam time), therefore, increases the percentage of the blood pool receiving a low dose. As shown in FIG. 4, the percent of the blood pool receiving 0.5 Gy was less with higher dose rates at the beginning of treatment. However, once 30 fractions have been administered, the percentage of blood receiving 0.5 Gy approached 100% for all dose rates tested. Only minor dose-rate-dependent differences were observed when using the mean dose as an endpoint; a mean dose of 2.2 Gy was calculated for both 600 MU/min and 1,200 MU/min plans, while a mean dose of 3.1 Gy was calculated for 300 MU/min plans.

In one embodiment, the present method may be used to compare dose to the blood pool for different treatment techniques, such as IMRT and 3D-conformal treatment techniques. For example, when IMRT and 3D-conformal treatment techniques were compared, Applicants found that by the end of a 60 Gy plan administered in 30 2-Gy fractions to an 8-cm diameter PTV, no differences were observed in the mean dose to the blood pool or in the proportion of blood receiving 0.5 Gy. Mean dose to the blood pool was 2.4 Gy for the tested 3D-conformal plan and 2.7 Gy for the tested IMRT plan. In both cases, nearly all of the blood received at least 0.5 Gy after 30 2-Gy fractions.

Figure 5:
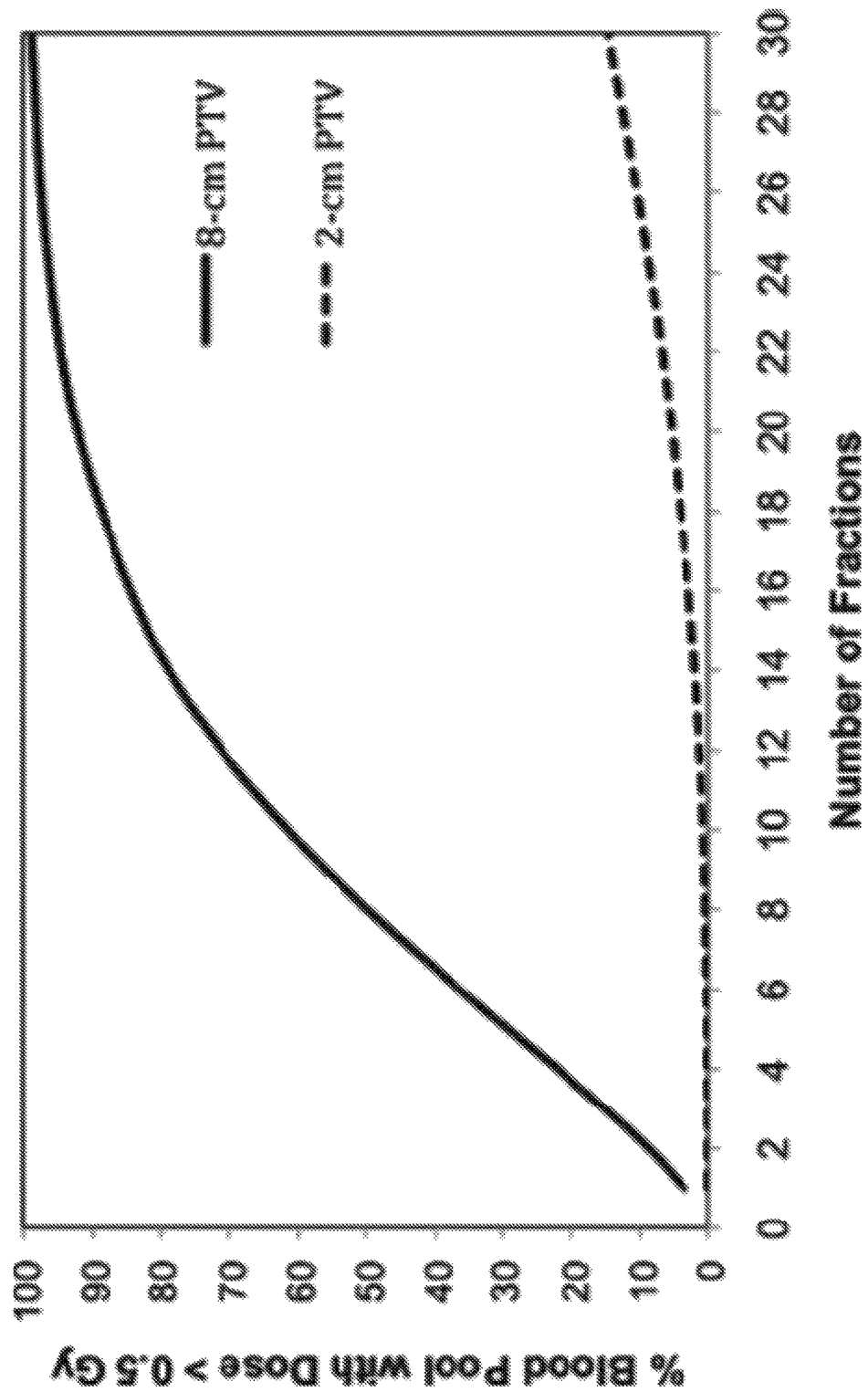
FIG. 5 is a graph showing percent of blood receiving >0.5 Gy with varying PTV sizes of 2-cm diameter (4.2 $cm^3$) and 8-cm diameter (268 $cm^3$). Dose rate=600 MU/min; 2 Gy/fraction.

FIG. 5 is a graph showing percent of blood receiving >0.5 Gy with varying PTV sizes of 2-cm diameter (4.2 cm³) and 8-cm diameter (268 cm³). Dose rate=600 MU/min; 2 Gy/fraction.

Major differences in target volume size may have a significant impact on the mean dose to the blood pool, particularly at higher doses (See FIG. 4). For a 60-Gy plan administered in 30 fractions, the mean blood dose was 2.2 Gy for an 8-cm diameter PTV but was 0.3 Gy for a 2-cm diameter PTV. These data were also analyzed in terms of the percent of blood receiving at least 0.5 Gy, as shown in FIG. 5. Smaller PTV size MAY decrease CBD. For a 2-cm diameter PTV (volume=4.2 cm3) receiving 60 Gy, 15% of the blood received 0.5Gy of radiation; however, for the 8-cm diameter PTV (volume=268 cm3), 99% of blood received Gy of radiation.

In one embodiment, Applicants have identified circulating blood as an organ at risk in radiation therapy by using the present method. Applicants found that standard treatment plans for brain tumors deliver potentially lymphotoxic radiation doses to the entire circulating blood pool. Altering dose rates or delivery techniques are unlikely to significantly affect DCC by the end of treatment. Applicants' result by using the present invention shows that novel approaches may be needed to limit radiation to circulating lymphocytes given the association of lymphopenia with poorer survival in patients with high grade gliomas (HGG).

In another configuration, the present invention discloses a computer system for calculating the radiation dose received by circulating blood cells such as lymphocytes. The computer system may use the methods as discussed above to calculate the radiation dose received by circulating blood cells such as lymphocytes.

The computer system may include a non-transitory, computer readable storage medium having instructions stored thereon that, when executed by a computer processor, cause the computer processor to undertake the steps of creating a tumor volume within the site using the medical imaging data; determining a dose of radiation delivered to the site using the tumor volume; generating a three-dimensional dose grid for the site; calculating a mean dose of radiation to a blood pool within the site; and quantifying a total volume of blood receiving radiation.

Figure 6:
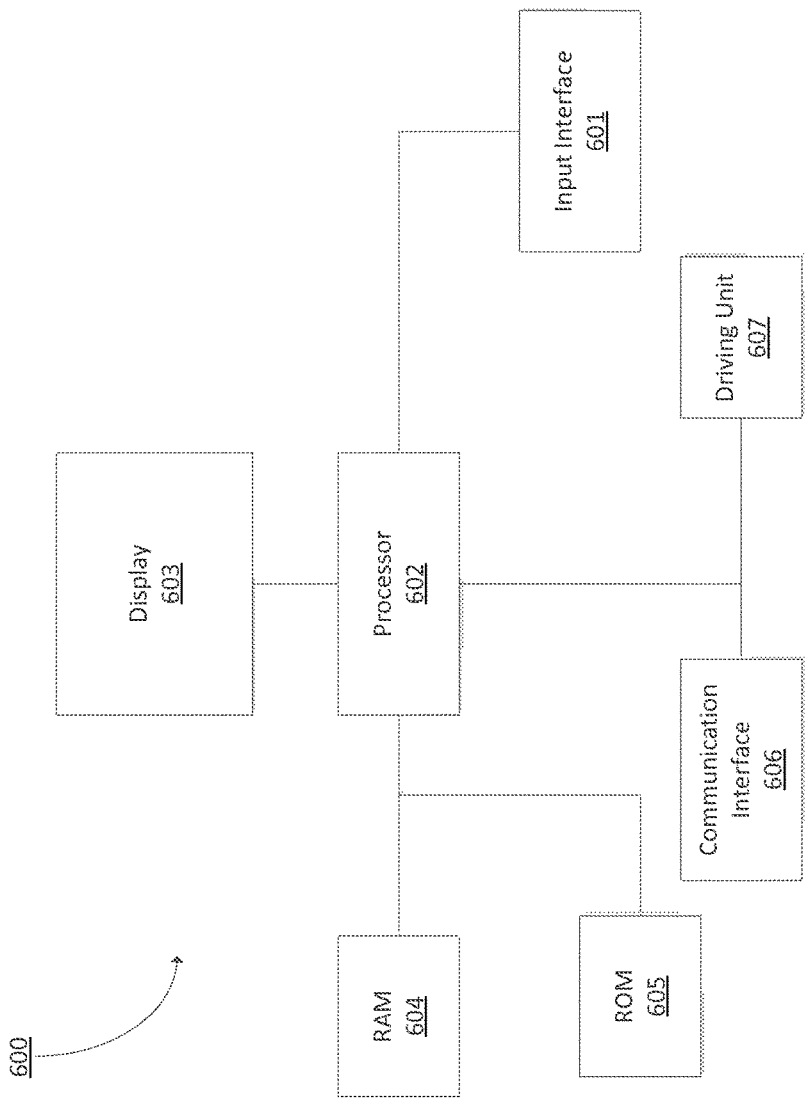
FIG. 6 is a block diagram showing a computer system for calculating radiation doses received by circulating blood cells according to one embodiment of the present invention.

FIG. 6 is a block diagram showing an exemplary computer system for calculating the radiation dose received by circulating blood cells such as lymphocytes consistent with the disclosed embodiments. As shown in FIG. 6, a computer system 600 for calculating the radiation dose received by circulating blood cells may include an input interface unit 601, a processor 602, a display device 603, a random access memory (RAM) unit 604, a read-only memory (ROM) unit 605, a communication interface 606, and a driving unit 607. Other components may be added and certain devices may be removed without departing from the principles of the disclosed embodiments.

Through the input interface unit 601, a pre-obtained medical imaging data such as CT scan or MRI information of a site in a patient may be entered into the system. The present computer system may be applicable for calculating the radiation dose received by circulating blood cells of any suitable sites in a patient. In one specific embodiment, the suitable site may be head, heart, lung, and others. In one specific embodiment, a suitable site may be head.

For this purpose, the input interface unit 601 may include any suitable data input means as understood by a person having ordinary skill in the art. For example, the input interface unit 601 may include any appropriate input device, one or more mass storage devices for storing data.

After pre-obtained medical imaging data such as CT scan or MRI information of a site in a patient is entered, the processor 602 in the computer system may operate under instructions of software programs, such as a first program and a second program to calculate radiation doses received by circulating blood cells. As discussed above, the first program may be a commercially available program such as the Pinnacle™ radiation treatment planning system (Version 9.0, Philips Inc., Madison, Wis.). Under the instruction of the first program, the processor 602 may create a tumor volume with a specific shape, e.g., spherical, calculate dose to the site, delineate the entire site and generate a three-dimensional dose grid for the site.

As discussed above, in one specific example, the second program may be an in-house software program, for example that written in MATLAB (version R2011b, Mathworks, Inc., Natick, Mass.). Under the instruction of the second program, the processor 502 may analyze the three-dimensional dose grid for the site and calculate a mean dose to the total blood pool and quantify the total volume of blood receiving radiation. Under the first and second programs, the processor 502 may also model the radiation dose delivered to circulating blood. Some of the results are shown in FIGS. 3-5.

In one embodiment, the computer processor may further undertake the step of generating a report indicating the quantity of radiation received by circulating blood within the subject.

In one embodiment, many subject/treatment-specific variables may be considered. Some of the variables may include target volume size associated with the dose of radiation, a radiation treatment technique associated with the dose of radiation, a dose rate associated with the dose of radiation, a total dose associated with the dose of radiation, a fraction size associated with the dose of radiation, a treatment time associated with delivering the dose of radiation, a speed of circulating blood within the subject, and a presence of vasculature relative to the treatment site.

In one embodiment, the subject/treatment-specific variables may include target volume size and number of radiation fractions as key predictors of dose to circulating blood.

In one embodiment, the computer processor under instructions of computer readable storage mediums may further undertake the step of generating a report indicating the quantity of radiation received by circulating blood within the subject.

In one embodiment, the computer processor under instructions of computer readable storage mediums may further undertake the step of determining organs within the subject that are at risk of being subjected to an undesired dose of radiation due to the radiation received by circulating blood within the subject.

In one embodiment, the computer processor under instructions of computer readable storage mediums may further undertake the steps of creating a tumor volume within the site using the medical imaging data; determining a dose of radiation delivered to the site using the tumor volume; generating a three-dimensional dose grid for the site; using the three-dimensional dose grid for the site, calculating a mean dose of radiation to a blood pool within the site; and quantifying a total volume of blood receiving radiation.

For this purpose, the processor 502 may operate under the instruction of non-transitive a computer-readable program or media. A computer-readable program or media for operating a processor is well known to a person having ordinary skill in the art. Processors suitable for the execution of a computer program include, by way of example, both general and special purpose microprocessors, and any one or more processors of any kind of digital computer. The processor 502 may include any appropriate type of graphic processing unit (GPU), general-purpose microprocessor, digital signal processor (DSP) or microcontroller, and application specific integrated circuit (ASIC), and the like. The processor 502 may execute sequences of computer program instructions to perform various processes associated with the calculation of radiation doses received by circulating blood cells as discussed above and following hereafter.

Generally, a processor will receive instructions and data from a read only memory (ROM) or a random access memory (RAM) or both. The essential elements of a computer are a processor for performing actions in accordance with instructions and one or more memory devices for storing instructions and data. In one embodiment of the present invention, the computer program instructions for the calculation of radiation doses received by circulating blood cells (for example, the first and the second programs) may be loaded into RAM 504 for execution by the processor 502 from the read-only memory (ROM) 505. Devices suitable for storing computer program instructions and data may also include all forms of non-volatile memory, media, and memory devices, including by way of example semiconductor memory devices, for example, EPROM, EEPROM, and flash memory devices; magnetic disks, for example, internal hard disks or removable disks; magneto optical disks; and CD ROM and DVD-ROM disks.

The present invention has been described in terms of one or more preferred embodiments, and it should be appreciated that many equivalents, alternatives, variations, and modifications, aside from those expressly stated, are possible and within the scope of the invention.

We claim:

1. A non-transitory, computer readable storage medium having instructions stored thereon that, when executed by a computer processor, cause the computer processor to:
   receive medical imaging data from a subject including information about a treatment site receiving a dose of radiation;
   receive a plurality of subject/treatment-specific variables including at least two of a target volume size associated with the dose of radiation, a radiation treatment technique associated with the dose of radiation, a dose rate associated with the dose of radiation, a total dose associated with the dose of radiation, a fraction size associated with the dose of radiation, a treatment time associated with delivering the dose of radiation, a speed of circulating blood within the subject, and a presence of vasculature relative to the treatment site; and
   determine using the plurality of subject/treatment-specific variables a quantity of radiation received by circulating blood within the subject when receiving the dose of radiation.

2. The computer readable storage medium of claim 1, further comprising generating a report indicating the quantity of radiation received by circulating blood within the subject.

3. The computer readable storage medium of claim 1, further comprising determining organs within the subject that are at risk of being subjected to an undesired dose of radiation due to the radiation received by circulating blood within the subject.

4. The computer readable storage medium of claim 1, further comprising creating a tumor volume within the site using the medical imaging data.

5. The computer readable storage medium of claim 4, further comprising determining a dose of radiation delivered to the site using the tumor volume.

6. The computer readable storage medium of claim 5, further comprising determining a dose of radiation delivered to the site using the tumor volume.

7. The computer readable storage medium of claim 6, further comprising generating a three-dimensional dose grid for the site.

8. The computer readable storage medium of claim 7, further comprising using the three-dimensional dose grid for the site, calculating a mean dose of radiation to a blood pool within the site.

9. The computer readable storage medium of claim 8, further comprising quantifying a total volume of blood receiving radiation.

10. A method for calculating radiation doses received by circulating blood cells in a patient comprising the steps of:
    a) obtaining medical imaging data of a site in a patient;
    b) creating a tumor volume within the site using the medical imaging data;
    c) determining a dose of radiation delivered to the site using the tumor volume;
    d) generating a three-dimensional dose grid for the site;
    e) using the three-dimensional dose grid for the site, calculating a dose of radiation to a blood pool within the site;
    f) quantifying a dose relationship in a dose volume histogram; and
    g) generating a report indicating the dose of radiation received by circulating blood using the quantification in step f).

11. The method of claim 10, wherein the tumor volume is spherical.

12. The method of claim 10, wherein step e) includes determining a size of the tumor volume and number of radiation fractions received by the tumor volume.

13. The method of claim 12, wherein step f) includes applying a model that uses radiation fractions received by the tumor volume to quantify the total volume of blood receiving radiation.

14. The method of claim 10, further comprising determining a radiation treatment technique used to deliver the dose of radiation, a dose rate used to deliver the dose of radiation, a treatment time used to deliver the dose of radiation, a speed of circulating blood within the subject, and a of major vasculature proximate to at least one of the tumor volume and the site.

15. The method of claim 10, wherein the medical imaging data includes at least one of magnetic resonance imaging (MRI) data and computed tomography (CT) data.

16. A computer system for calculating radiation doses received by circulating blood cells in a patient, the computer system comprising:
    a) an input interface unit to load pre-obtained medical imaging data of a site in a patient into the system,
    b) a processor configured to carry on the steps of:
       (1) creating a tumor volume within the site using the medical imaging data;
       (2) determining a dose of radiation delivered to the site using the tumor volume;
       (3) generating a three-dimensional dose grid for the site;
       (4) calculating a dose of radiation to a blood pool within the site;
       (5) quantifying a total volume of blood receiving radiation; and
    c) a display to display a report of radiation doses received by circulating blood cells in a patient.

17. The computer system of claim 16, wherein the tumor volume is spherical.

18. The computer system of claim 16, wherein step 4) includes determining a size of the tumor volume and number of radiation fractions received by the tumor volume.

19. The computer system of claim 16, wherein step 5) includes applying a model that uses radiation fractions received by the tumor volume to quantify the total volume of blood receiving radiation.

20. The computer system of claim 16, wherein the steps carried by the processor further comprising determining a radiation treatment technique used to deliver the dose of radiation, a dose rate used to deliver the dose of radiation, a treatment time used to deliver the dose of radiation, a speed of circulating blood within the subject, and a major vasculature proximate to at least one of the tumor volume and the site.

21. The computer system of claim 16, wherein the medical imaging data includes at least one of magnetic resonance imaging (MRI) data and computed tomography (CT) data.

* * * * *